US009469913B2

(12) United States Patent
Oberlitner et al.

(10) Patent No.: US 9,469,913 B2
(45) Date of Patent: Oct. 18, 2016

(54) CLOSED LOOP ELECTROLYTE ANALYZER

(71) Applicant: APPLIED Materials, Inc., Santa Clara, CA (US)

(72) Inventors: Thomas H. Oberlitner, Kalispell, MT (US); Cameron H. Law, Kalispell, MT (US); Justin Boucher, Kalispell, MT (US)

(73) Assignee: APPLIED Materials, Inc., Santa Clara, CA (US)

( * ) Notice: Subject to any disclaimer, the term of this patent is extended or adjusted under 35 U.S.C. 154(b) by 154 days.

(21) Appl. No.: 14/527,493

(22) Filed: Oct. 29, 2014

(65) Prior Publication Data

US 2015/0159293 A1    Jun. 11, 2015

Related U.S. Application Data

(60) Provisional application No. 61/912,489, filed on Dec. 5, 2013.

(51) Int. Cl.
| | |
|---|---|
| *C25D 21/12* | (2006.01) |
| *C25D 21/14* | (2006.01) |
| *G01N 27/42* | (2006.01) |
| *G01N 27/416* | (2006.01) |

(52) U.S. Cl.
CPC ............... *C25D 21/14* (2013.01); *G01N 27/42* (2013.01); *G01N 27/4166* (2013.01)

(58) Field of Classification Search
CPC .... C25D 21/14; C25D 21/12; C25D 17/001; C25D 21/18; C25D 21/04; C25D 21/06; C25D 17/00; C25D 5/006; C25D 17/002; C25D 5/08; G01N 27/42; G01N 27/4166; G01N 27/48; G01N 31/164; G01N 27/49
See application file for complete search history.

(56) References Cited

U.S. PATENT DOCUMENTS

| | | | |
|---|---|---|---|
| 6,458,262 B1 | 10/2002 | Reid | |
| 6,551,479 B1 | 4/2003 | Graham et al. | |
| 6,592,736 B2 | 7/2003 | Fulton et al. | |
| 6,814,855 B2 | 11/2004 | Graham et al. | |
| 6,986,835 B2 | 1/2006 | Balisky et al. | |
| 7,005,046 B2 | 2/2006 | Stevens et al. | |
| 7,229,543 B2 | 6/2007 | Graham et al. | |
| 8,372,258 B2 | 2/2013 | Willey et al. | |
| 2003/0201191 A1 | 10/2003 | Kovarsky et al. | |
| 2005/0053522 A1* | 3/2005 | King ...................... | C25D 21/12 422/68.1 |

\* cited by examiner

*Primary Examiner* — Xiuyu Tai
(74) *Attorney, Agent, or Firm* — Kenneth H. Ohriner; Perkins Coie LLP

(57) ABSTRACT

A processing system for electroplating semiconductor wafers and similar substrates includes an electrolyte tank, at least one processing chamber connected to the electrolyte tank via fluid lines, and an electrolyte analyzer. The electrolyte analyzer may have a probe, such as a voltammetry probe, in the electrolyte tank, a pump, a reservoir and at least one valve, with these components connected via fluid lines to form a fluid loop. The valve may be switchable to provide a closed fluid loop where electrolyte circulates through the probe to analyze the electrolyte, and to provide an open fluid loop to removal of the used electrolyte and introduction of fresh electrolyte from the tank into the fluid loop. The used electrolyte may be moved to a facility drain and not returned to the electrolyte tank, to reduce risk of contamination.

12 Claims, 3 Drawing Sheets

CLOSED LOOP ELECTROLYTE ANALYZER

This Application claims priority to U.S. Provisional Patent Application No. 61/912,489 filed Dec. 5, 2013, and incorporated herein by reference.

FIELD OF THE INVENTION

The field of the invention is systems and methods for electroplating semiconductor material wafers and similar types of substrates. The invention also is directed to an electrolyte analyzer for use in these types of systems.

BACKGROUND OF THE INVENTION

Microelectronic devices such as semiconductor devices are generally fabricated on and/or in substrates or wafers. In a typical fabrication process, one or more layers of metal or other conductive materials are formed on a wafer in an electroplating processor. The processor has a bath of electrolyte held in vessel or bowl, with one or more anodes in the bowl. Due to their microscopic size and chemical and electrical characteristics, microelectronic devices are highly sensitive to particle and chemical contamination. Consequently, the electrolyte must remain free of contamination, and have a chemical makeup within specified limits. Monitoring the chemical constituents and concentrations is important because variations in the electrolyte may degrade plating quality.

Electrolyte analysis systems have been developed for this purpose. These systems typically use voltammetry measurement techniques. One example of an electrolyte analysis system, as used for copper damascene electrolyte, is the Real Time Analysis system (RTA) available from Technic Inc., Inc., Cranston, R.I., USA. Similar systems are available from other manufacturers. These types of systems determine concentrations of inorganic constituents and organic additives in the electrolyte via AC and DC voltammetry analysis, using an electrode probe immersed in the electrolyte. However, the probe is highly sensitive to temperature and flow rate. Consequently, in the past use of these types of probes has required extensive use of various heat exchangers, insulated lines and other temperature control techniques, and a large buffer volume of electrolyte. The voltammetry process itself may apparently also create small copper particles in the electrolyte which may act as a contamination source. As a result, engineering challenges remain in designing improved electrolyte monitoring systems.

BRIEF DESCRIPTION OF THE DRAWINGS

In the drawings, the same reference number indicates the same element in each of the views.

DETAILED DESCRIPTION OF THE DRAWINGS

Figure 1:
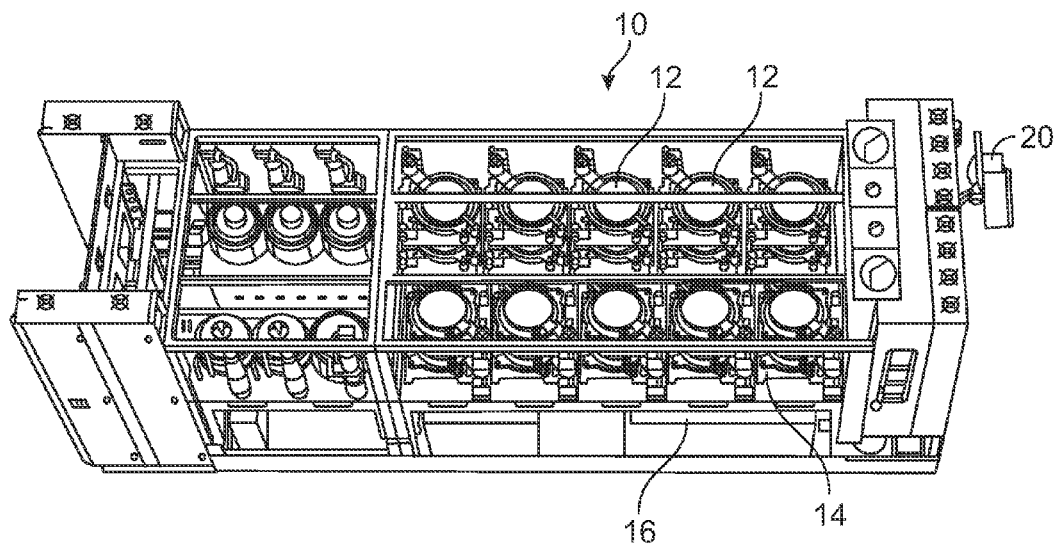
FIG. 1 is a top perspective view of an electroplating system.

As shown in FIG. 1, an electroplating system 10 may include multiple processing chambers 12 supported on a deck 14. The chambers 12 may be supplied with electrolyte from a bulk electrolyte tank 16. The electroplating system 10 is typically controlled via a computer controller 20.

Figure 2:
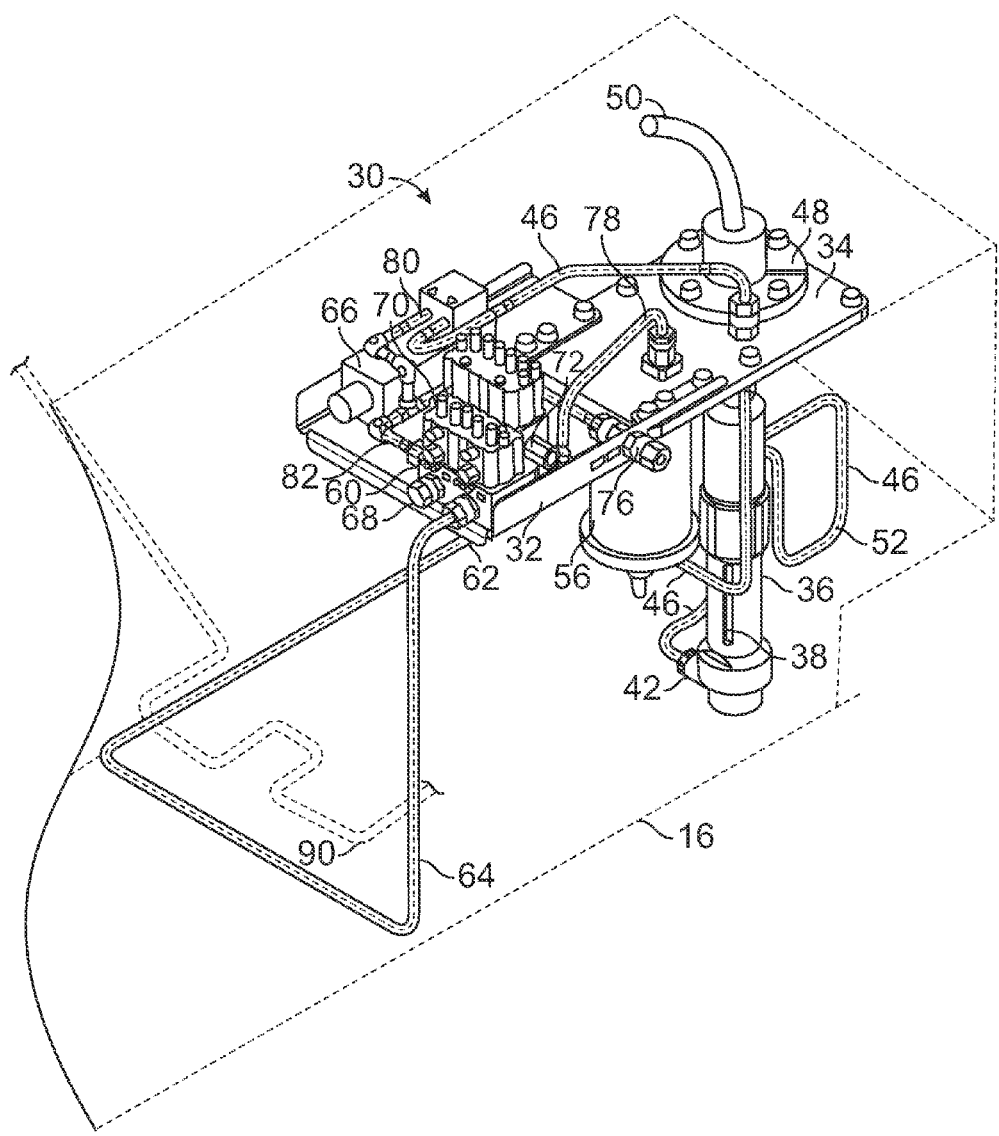
FIG. 2 is a top and left side perspective view of a closed loop electrolyte analyzer which may be used in the system shown in FIG. 1.
Figure 3:
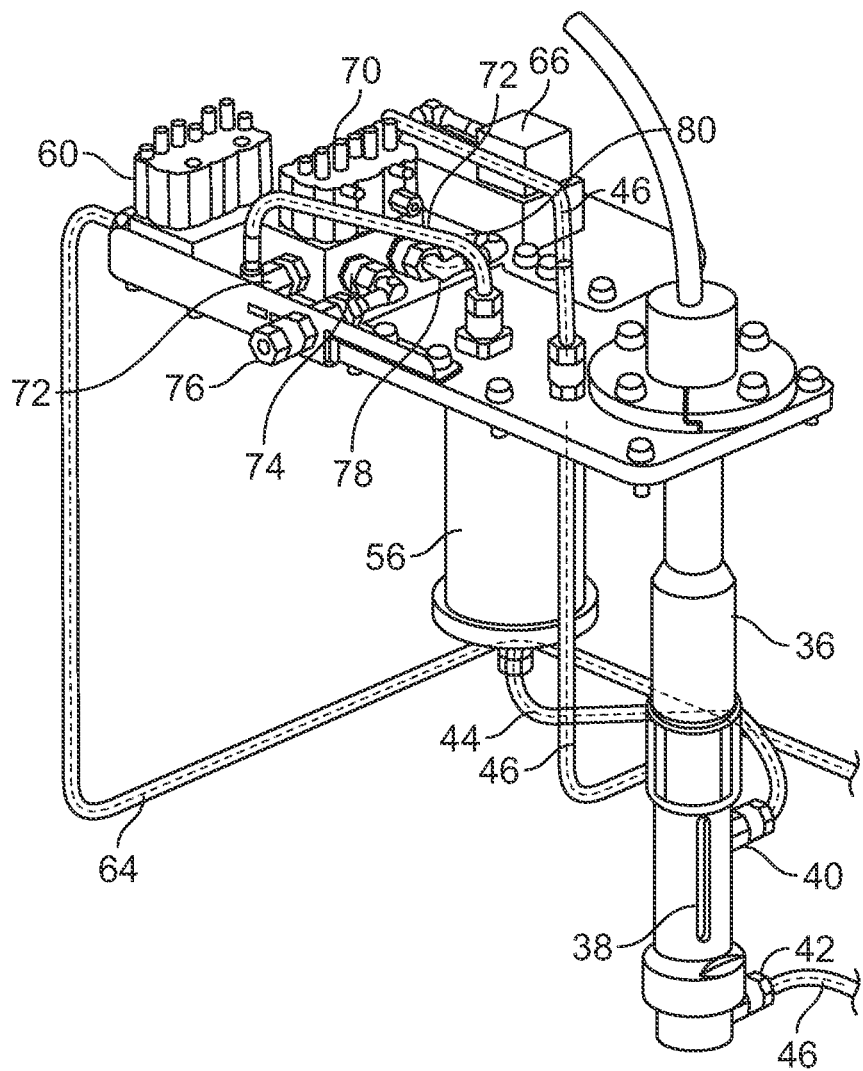
FIG. 3 is a top and right side perspective view of the closed loop electrolyte analyzer shown in FIG. 2.

FIGS. 2-3 show a electrolyte analysis system 30 which unlike previous electrolyte analysis systems, is a closed loop system. A small volume of test electrolyte is introduced into the electrolyte analysis system 30 from the bulk electrolyte in the tank 16 and is used to conduct the electrolyte analysis. When the analysis is completed, the small volume of test electrolyte is not returned to the tank 16. Rather the used test electrolyte is moved to a facility drain and it is not reused. This reduces potential for contamination of the bulk electrolyte used in plating operations.

The bulk electrolyte in the tank 16 is often heated or cooled to maintain an electrolyte temperature within a specified range, usually in the range of 18-25° C. This temperature control may be achieved by flowing a heated or cooled liquid (such as water) through coils 90 submerged in the electrolyte in the tank. In the electrolyte analysis system 30, the probe is submerged in the tank 16, and the probe inlet or supply line may be provided with coils 52 as well, to provide liquid-to-liquid heat transfer between the bulk electrolyte in the tank 16 and the test electrolyte flowing into the probe. This design allows for close temperature control of the test electrolyte without the need for insulated fluid lines and extensive supplemental heating and cooling apparatus.

Turning in detail now to FIGS. 2 and 3, the present electrolyte analysis system 30, includes a probe 36 attached to a lid 34 or other structure optionally using a collar 48. An electrode section 38 may be located at the lower end of the probe 36, optionally close to the bottom of the tank 16. An electrical cable 50 extending out of the top end of the probe contains power and signal lines (wires) connecting to the probe computer supplied with the probe from the probe manufacturer.

A supply valve 60 and an circulation valve 70 are connected to a pump 66, supported on the lid 34 or on a tray 32 attached to the lid 34. The lid may rest on top of the tank 16, with the probe 36 and other components extending down into the tank 16 through a top opening of the tank 16.

As shown in FIG. 3, a reservoir 56 may be attached to a bottom surface of the lid or tray and extend down into the tank 16. Probe suppliers may specify a minimum volume of electrolyte necessary for accurate voltammetry analysis. The reservoir, if used, may be sized to hold a volume of electrolyte, that in combination with the volume of electrolyte contained in the rest of the electrolyte analysis system 30, amounts to a total volume meeting the probe supplier's specifications. A probe inlet line 46 connects an outlet 40 of the pump 66 to a probe inlet 42. As shown in FIG. 2 a pump line 80 leads to a T-connection branched to an outlet 82 of the supply valve 60 and to an outlet 72 on the circulation valve 70.

The circulation valve 70 is switchable between a circulation position, where the circulation line 78 connects to the pump line 80 through the circulation valve 70, and a drain position where the circulation line 78 connects to the drain port 76. A drain line (not shown) runs from the drain port 76 to a facility drain.

As shown in FIG. 2, a tank inlet line 64 may be connected to a tank inlet port 62 on the supply valve 60, to provide fresh test volumes of electrolyte from the tank 16 to the analyzer system 30. The supply valve 60 may also optionally include a control sample inlet 68 to allow a control test volume of electrolyte to be manually introduced into the analyzer system 30. This allows for calibration of the analyzer system 30 using a control test volume of anolyte provided manually from a source separate from the electrolyte in the tank 16. The supply valve 60 is switchable from a first position where the tank inlet line 64 is connected to the T-connection, to a second position where the control sample inlet 68 is connected to the T-connection. The supply valve may also have a closed position where the outlet 82 is closed off.

In use, the analyzer 30 may be supported on and/or attached onto the top of the tank 16, with the probe 36, the reservoir 56, and the probe inlet and outlet lines submerged in electrolyte in the tank 16. To provide an initial volume of electrolyte into the analyzer 30, the supply valve is switched to the first position and the pump 66 is turned on. Using a positive displacement pump, electrolyte is drawn into the pump 66 and then pumped into the probe 36 via the probe inlet line 46. With continued pumping, the probe 36, the reservoir 56, the connections lines, and the circulation valve 70 are filled with electrolyte. Optionally, the circulation valve 70 may be switched into the second position during this fill process. In this case, a flow of electrolyte from the drain fitting 76 will indicate that the analyzer 30 is filled with electrolyte.

The supply valve 60 may be switched to an off position where the outlet 82 is not connected to either of the other lines on the supply valve. The circulation valve 70 is set to the first position, forming a closed electrolyte circulation loop. The pump 66 continues to circulate electrolyte through the closed loop, under the control of the processing system controller 20, or the computer provided with the probe 36 by the probe supplier. Depending on the electrolyte characteristics and the probe type, voltammetry measurements on the closed loop of circulating electrolyte may continue for a predetermined time interval, for example, from 1 to 2, 4 or 8 hours. The voltammetry measurements provide various types of information on the chemical characteristics of the electrolyte. These may be used to determine adjustments to be made to the electrolyte and/or to the electroplating process.

After the predetermined time interval, the electrolyte in the analyzer 30 is replaced. The circulation valve 70 is switched to the drain position and the supply valve 60 is in or remains in the off position. With the pump 66 running, electrolyte within the analyzer is pumped out to a facility drain via the drain fitting 76. Then the supply valve 60 is switched to the first position to allow the pump to draw fresh electrolyte from the tank 16 into the analyzer. After the analyzer 30 is filled with fresh electrolyte, the supply valve 60 is closed, and the circulation valve is switched to the circulation position. The analyzer 30 is then ready to resume monitoring via the probe 36. In a typical design, the volume of liquid in the analyzer may be reduced to 100 to 250, 500 or 1000 ml. This reduces the consumption of electrolyte associated with operation of the probe 36.

Probe calibration or other probe operations may periodically require a control volume of electrolyte specifically provided for this purpose. To introduce the control volume of electrolyte into the analyzer 30, any used electrolyte in the analyzer is pumped out to the drain as discussed above. A suction tube of the container holding the control volume is engaged into the control sample inlet 68 with the supply valve switched to the second position. The pump 66 then draws the control sample into the analyzer 30 and the valves are switched to provide a closed loop containing the control sample, in the same way as described above relative to providing a fresh volume of electrolyte from the tank 16 into the analyzer 30.

Briefly stated, a probe in a voltammetry system may be provided with a specified closed loop volume as may be required for proper probe operations. A small buffer volume may be in the tank either in the main volume of the catholyte or in the headspace above the catholyte. By using temperature-controlled catholyte, the bulk volume of the sample catholyte in the closed loop is maintained at the same temperature as the bulk catholyte. The fluid lines may be thin wall metal or plastic tubes, for improved heat transfer.

As shown in FIGS. 2-3, the length of fluid lines submerged in the electrolyte in the tank 16 is much greater than the length of the fluid lines above the tank. This increases heat transfer between the electrolyte in the tank and the electrolyte in the closed loop, and helps to keep the electrolyte in the closed loop at the desired temperature prior to analysis.

FIGS. 2-3 show one example of how the analyzer 30 may be designed. Various of the elements shown may be omitted or combined with another element, such as the tray 32, the lid 34, the control sample inlet 68, the reservoir 56 and others. The supply valve 60 and recirculation valve 70 may also be combined into a single valve. The configuration and interconnection of the various fluid lines may also be modified depending on the system requirements. Where the process chambers 12 have separate catholyte and anolyte chambers, for example with a membrane between them, the tank 16 typically contains catholyte, and the description of electrolyte above then refers to catholyte.

As used in the claims below, the term connected at least indirectly means connected directly relative to fluid flow, i.e., with no intervening element, or connected indirectly, i.e., with one or more intervening elements. In addition, the term connected means connected in the sense of fluid movement from one element to another element, and not necessarily physically connected or attached. Closed fluid loop means a continuous loop that the electrolyte circulates through. Open fluid loop means a valve or port in the fluid loop is open to allow used electrolyte to be removed from the analyzer, and/or to allow fresh electrolyte to be introduced into the analyzer.

A method for analyzing electrolyte in a processing system may include the steps of: positioning an electrode section of a voltammetry probe into a tank of electrolyte; opening a first valve and pumping electrolyte from the tank into a fluid loop of an analyzer until the fluid loop is substantially filled, usually with about 200-500 mL of electrolyte; closing the first valve to provide a closed fluid loop; cycling electrolyte within the closed fluid loop while performing voltammetry measurements, opening a second valve and pumping the used electrolyte out of the fluid loop and into a drain line; closing the second valve and refilling the fluid loop with fresh electrolyte from the tank. Electrolyte within the fluid loop may be heated or cooled by flowing in an extended or coiled path in the tank electrolyte, before flowing into the probe. A control volume of electrolyte may be periodically manually provided into the fluid loop, instead of the tank electrolyte, by switching the first valve to a second position and drawing the control electrolyte in via the pump.

Thus, novel systems and methods have been described. Various changes and substitutions may of course be made without departing from the spirit and scope of the invention. The invention, therefore, should not be limited, except to the following claims and their equivalents

The invention claimed is:
1. A processing system, comprising:
an electrolyte tank;
at least one processing chamber connected to the electrolyte tank via processing chamber fluid lines;

an electrolyte analyzer including a probe at least partially within the electrolyte tank, a pump, a valve switchable to a first position and to a second position, and probe fluid lines connecting the probe at least indirectly to the pump and to the valve, with the pump, the valve, the probe and the probe fluid lines forming a fluid loop, which is a closed fluid loop when the valve is in the first position, and which is an open fluid loop when the valve is in the second position.

2. The processing system of claim 1 further comprising a reservoir in the fluid loop.

3. The processing system of claim of claim 2 with the reservoir and the probe both substantially entirely within the electrolyte tank.

4. The processing system of claim 1 with the length of the probe fluid lines in the tank greater than the length of probe fluid lines not in the tank.

5. The processing system of claim 2 with the probe, the reservoir, the pump and the valve supported on a plate on a top surface of the electrolyte tank.

6. A processing system, comprising:
an electrolyte tank;
at least one processing chamber connected to the electrolyte tank via processing chamber fluid lines;
an electrolyte analyzer including a fluid loop having a probe at least partially within the electrolyte tank, a pump, a reservoir, a supply valve and a circulation valve, with the circulation valve switchable to a first position, wherein the fluid loop is a closed loop to allow electrolyte to continuously cycle through the probe, to a second position, wherein the fluid loop is an open loop, to allow electrolyte to be pumped out of the fluid loop; and
with the supply valve switchable to a first position, wherein the fluid loop is an open loop, to supply fresh electrolyte into the fluid loop, and to a second position wherein the supply valve is closed to prevent any electrolyte from flowing through the supply valve.

7. The processing system of claim 6 with the supply valve switchable to a third position where a control sample port on the supply valve is connected to an inlet port of the pump.

8. The processing system of claim 6 wherein the pump is a positive displacement pump.

9. The processing system of claim 6 further including heating/cooling coils in the tank connected to a source of heated or chilled liquid.

10. The processing system of claim 6 with the fluid loop having a volume of 200 to 500 mL.

11. An electrolyte analyzer, comprising:
a voltammetry probe, a positive displacement pump, a reservoir, a supply valve and a circulation valve;
the circulation valve having an inlet port connected to an outlet port of the reservoir, a drain port connected to a drain line, and a circulation port connected to an inlet port of the pump, with the circulation valve switchable from a first position wherein the inlet port of the circulation valve is connected to the circulation port, and a second position wherein the inlet port of the circulation valve is connected to the drain port;
the probe having a probe outlet port connected to an inlet port of the reservoir and a probe inlet port connected to an outlet port of the pump;
the supply valve having a first inlet port, a second inlet port, and an outlet port connected to the inlet port of the pump, with the supply valve switchable from a first position wherein the first inlet port is connected to the outlet port of the supply valve, and a second position wherein the second inlet port is connected to the outlet port of the supply valve.

12. The electrolyte analyzer of claim 11 with the reservoir and the probe extending down from a bottom surface of a support tray, and with the pump, the circulation valve and the supply valve mounted on a top surface of the support tray.

* * * * *